(12) United States Patent
Kirl et al.

(10) Patent No.: US 12,714,731 B2
(45) Date of Patent: Aug. 25, 2026

(54) PRODUCTION OF A PROBIOTIC COMPOSITION

(71) Applicant: Bluestone Pharma GmbH, Baar (CH)

(72) Inventors: Elisabeth Kirl, Bruck an der Mur (AT); Bernhard Hofbauer, Mürzzuschlag (AT); Michael Faber, Sitges (ES); Karsten Brandt, Sitges (ES)

(73) Assignees: BLUESTONE PHARMA GMBH, Baar (CH); BLIS TECHNOLOGIES LIMITED, Dunedin (NZ)

( * ) Notice: Subject to any disclaimer, the term of this patent is extended or adjusted under 35 U.S.C. 154(b) by 0 days.

(21) Appl. No.: 18/593,178

(22) Filed: Mar. 1, 2024

(65) Prior Publication Data

US 2024/0293479 A1 Sep. 5, 2024

(30) Foreign Application Priority Data

Mar. 3, 2023 (EP) .................................... 23159945

(51) Int. Cl.

| | |
|---|---|
| ***A61K 35/741*** | (2015.01) |
| ***A61K 9/19*** | (2006.01) |
| ***C12N 1/205*** | (2026.01) |
| ***C12R 1/46*** | (2006.01) |

(52) U.S. Cl.

CPC .............. *A61K 35/741* (2013.01); *A61K 9/19* (2013.01); *C12N 1/205* (2021.05); *C12N 2500/16* (2013.01); *C12N 2500/34* (2013.01); *C12N 2500/38* (2013.01); *C12N 2500/50* (2013.01); *C12N 2500/74* (2013.01);
(Continued)

(58) Field of Classification Search

CPC ...... A61K 35/741; A61K 9/19; A61K 35/744; C12N 1/205; C12N 2500/16; C12N 2500/34; C12N 2500/38; C12N 2500/50; C12N 2500/74; C12N 2500/84; C12N 2501/998; C12N 1/20; C12N 1/02; C12N 1/04; C12N 1/38; C12R 2001/46; A23L 33/135; A23L 2/382; A23L 2/52; A23G 3/366; A23G 4/123; A23V 2002/00; A23V 2200/3204

See application file for complete search history.

(56) References Cited

U.S. PATENT DOCUMENTS

2014/0023620 A1 1/2014 Ioudina

FOREIGN PATENT DOCUMENTS

CN 107365705 B 1/2021
CN 115261263 A 11/2022

(Continued)

OTHER PUBLICATIONS

Barbour et al., PLOS One, vol. 9 (6), e100541—Jun. 2014, p. 1-16. (Year: 2014).*

(Continued)

*Primary Examiner* — Robert B Mondesi
*Assistant Examiner* — Naghmeh Nina Moazzami
(74) *Attorney, Agent, or Firm* — MH2 Technology Law Group LLP

(57) ABSTRACT

Provided is a method of producing a freeze-dried probiotic composition as well as a method of producing a probiotic raw material which involves culturing of a *Streptococcus salivarius* strain. Furthermore, a corresponding probiotic composition and a corresponding probiotic raw material is provided.

25 Claims, 2 Drawing Sheets

(52) U.S. Cl.
CPC .... *C12N 2500/84* (2013.01); *C12N 2501/998* (2013.01); *C12R 2001/46* (2021.05)

(56) References Cited

FOREIGN PATENT DOCUMENTS

| | | | |
|---|---|---|---|
| EA | 031179 | B1 | 11/2018 |
| EA | 201391067 | A1 | 11/2018 |
| RU | 2260041 | C2 | 9/2005 |
| RU | 2605626 | C2 | 12/2016 |
| RU | 2698032 | C1 | 8/2019 |
| WO | 2003070919 | A1 | 8/2003 |
| WO | 2011110884 | A1 | 9/2011 |
| WO | 2012098254 | A1 | 7/2012 |

OTHER PUBLICATIONS

Hutkins et al., pH Homeostasis in Lactic Acid Bacteria, Journal of Dairy Science vol. 76: 8, 1993, p. 2354-2365. (Year: 1993).*

Medrano et al., Effect of Acid Shock with Hydrochloric, Citric, and Lactic Acids on the Survival and Growth of *Salmonella typhi* and *Salmonella typhimurium* in Acidified Media, Journal of Food Protection vol. 68, Issue 10, Oct. 1, 2005, pp. 2047-2053 (Year: 2005).*

Wall et al., The early response to acid shock in *Lactobacillus reuteri* involves the ClpL chaperone and a putative cell wall-altering esterase. Appl Environ Microbiol. Jun. 2007;73(12):3924-35 (Year: 2007).*

Ting et al., A simple substrate feeding strategy using a pH control trigger in fed-batch fermentation. Appl Biochem Biotechnol. Apr. 2008;149(1):89-98 (Year: 2008).*

European Search Report dated Sep. 4, 2023 for corresponding European Application No. 23159945.7, 5 pages.

Wescombe et al., "Developing oral probiotics from *Streptococcus salivarius*", Future Microbiol., 2012, vol. 7, No. 12, pp. 1355-1371.

Office Action dated Feb. 28, 2025 for corresponding Eurasian Patent Application No. 202490392, English translation only, 3 pages.

* cited by examiner

PRODUCTION OF A PROBIOTIC COMPOSITION

CROSS-REFERENCE TO RELATED APPLICATIONS

This application claims priority to European Application No. 23 159 945.7 filed 3 Mar. 2023, the entire disclosure of which is hereby incorporated by reference in its entirety.

FIELD OF THE INVENTION

The invention relates to a method of producing a freeze-dried probiotic composition as well as to a method of producing a probiotic raw material which involves culturing of *Streptococcus salivarius*, in particular *Streptococcus salivarius* K12, ENT-K12, M18, and M18DF. Furthermore, the invention is directed to a corresponding probiotic composition and a corresponding probiotic raw material as well as to their use in the production of probiotic products. The invention further relates to a method of culturing *Streptococcus salivarius*.

BACKGROUND OF THE INVENTION

Probiotics are defined as live microorganisms which when administered in adequate amounts confer a health benefit on the host. The beneficial effects of probiotics may be mediated by a direct antagonistic effect against specific groups of undesired organisms, resulting in a decrease of their numbers, by an effect on the metabolism of such groups of organisms or by a general stimulatory effect on the immune system of animal or human hosts. Probiotic microorganisms have been identified among microorganisms classified as yeasts, fungi and bacteria. For instance, lactic acid bacteria are in general recognized as being useful as probiotics or "probiotically active" organisms, i.e. organisms that may beneficially affect animal or human hosts.

The lactic acid bacterium *Streptococcus salivarius* is a pioneer colonizer of the human oral cavity and persists there as a predominant member of the native microbiota throughout the life of its human host. Many strains are producers of salivaricin, which are diverse in their activity spectra and are thought to play an important role in both stabilizing the oral microbiota and preventing overgrowth (or infection) by potential pathogens. *Streptococcus salivarius* K12 is a commonly used probiotic strain and is well suited for use as an upper respiratory tract probiotic due to its natural propensity to inhabit the human oral cavity and be strongly competitive with a number of potential pathogens.

Probiotics like *S. salivarius* K12 are administered in many different way, for example in the form of a tablet, in particular a lozenge or a chewable tablet, chewing gum, capsule, sachet or as food, drink, confectionary, or nutraceutical. Thus, *Streptococcus salivarius* needs to be produced in large scale and needs to be provided in a form suitable for further use, in particular for further processing into the above-mentioned probiotic products.

This problem is solved by the present invention in accordance with the embodiments as characterized in the claims and described further below.

SUMMARY OF THE INVENTION

The present invention relates to a method of producing a probiotic composition, which comprises large scale fermentation of a *Streptococcus salivarius* strain, preferably *S. salivarius* K12, ENT-K12, M18, or M18DF. In particular, the probiotic composition which is produced by the method of the present invention is a freeze-dried powder.

The method of the present invention comprises cultivation of a *Streptococcus salivarius* strain in growth medium comprising dextrose at pH 6.8 to 7.2, preferably at pH 7.1, until the concentration of dextrose reached 10-15 g/L. The method further comprises a step of lowering the pH when the concentration of dextrose reached 10-15 g/L, preferably the pH is lowered to 5, and more preferably to 5.1 to 5.5, over 30 min to 3 hours, preferably over 40 minutes to 1 hour, and a step of raising the pH again to a pH value between 6.8 and 7.2 until end of cultivation. End of cultivation is preferably reached as soon as the dextrose is used up, i.e. when the dextrose concentration is about 0 g/L. This pH lowering has the surprising effect that a higher cell-count and more stable cells can be achieved. Without intended to be bound by theory, it is prudent to expect that the pH stress eliminates damaged bacteria which leads to a more stable and viable cell culture.

In a preferred embodiment, the method of the present invention comprises cultivation at 30° C. to 37° C., preferably at 30° C. to 35° C., most preferably at 33° C. In a further preferred embodiment, the method of the present invention comprises cultivation in growth medium having an initial concentration of dextrose of 25 g/L to 40 g/L.

Preferably, the method of the present invention comprises cultivation with dissolve oxygen (DO) control and in a preferred embodiment, the DO concentration is kept between 50% and 80% in the first half of the cultivation, i.e. until the carbon source reaches 10 to 15 g/L and before the pH is lowered, and wherein the DO concentration is kept between 0% and 50% in the second half of the cultivation, i.e. when the carbon source concentration drops under 10 to 15 g/L.

The method of the present invention further comprises the concentration of the culture and mixing the concentrate with lyoprotectants, wherein the pH of the mixture is preferably adjusted to about 6.8 to 7.2. The method of the present invention further comprises freeze-drying of the mixture to obtain the freeze-dried probiotic composition, wherein freeze-drying is preferably performed for 72 hours. Optionally the mixture is milled and homogenized to a powder.

Since the composition is used for human consumption, the raw materials used for the cultivation of *S. salivarius* as well as the lyoprotectants should be safe for human consumption, for example have to have the GRAS (generally recognized as safe) status. GRAS is a United States Food and Drug Administration (FDA) designation that a chemical or substance added to food is considered safe by experts. Furthermore, it is preferred that the raw materials for cultivation and the lyoprotectants are not only safe for human consumption, but are also free of allergens and/or are pharmaceutical-grade and GMP (Good Manufacturing Practice) grade, respectively. A pharmaceutical grade compound can be defined as any active or inactive drug, biologic or reagent, for which a chemical purity standard has been established by a recognized national or regional pharmacopeia (e.g., the United States Pharmacopeia (USP).

In one embodiment, the growth medium used in the method of the present invention comprises dextrose, yeast extract, a milk product, preferably whey permeat, preferably wherein the growth medium further comprises casein peptone, an emulsifier, preferably polysorbate 80, a buffering agent, preferably di-potassium phosphate and an anti-foaming agent.

In another embodiment, the growth medium used in the method of the present invention comprises yeast extract and dextrose, but no milk products. In particular no whey permeat, milk skim milk powder or cascin-peptone is used. The growth medium preferably further comprises a buffering agent, preferably di-potassium phosphate, an emulsifier, preferably polysorbate 80, magnesium sulfate, manganese sulfate, and an anti-foaming agent.

As shown in Example 4, the presence of ascorbate has a further stabilizing effect on the cells. In particular, after storing of the composition for a certain amount of time (here exemplified by 30 days, 90 days and 180 days) at 4° C., the colonly forming units (CFUs) were higher when cells have been cultivated in growth medium comprising ascorbate compared to growth medium without ascorbate. Thus, the presence of ascorbate in the growth medium has a stabilizing effect.

Accordingly, in one embodiment, the growth medium used in the method of the present invention further comprises ascorbate.

In particular, in one embodiment, the growth medium comprises dextrose, yeast extract, a milk product, preferably whey permeat, and ascorbate, preferably wherein the growth medium further comprises casein peptone, an emulsifier, preferably polysorbate 80, a buffering agent, preferably di-potassium phosphate and an anti-foaming agent.

In one embodiment, the growth medium comprises yeast extract, dextrose and ascorbate, but no milk products as defined above, preferably wherein the growth medium further comprises a buffering agent, preferably di-potassium phosphate, an emulsifier, preferably polysorbate 80, magnesium sulfate, manganese sulfate, and an anti-foaming agent.

The lyoprotectants as used in the method of the present invention are preferably trehalose, lactitol monohydrate, and maltodextrin; or trehalose, dextrose, sodium ascorbate, sodium citrate and L-cystein.

All of those ingredients are safe for human consumption and can optionally be provided as pharmaceutical grade compounds. Furthermore, the growth medium which comprises no milk products as well as the mixture of lyoprotectants are even free of allergens.

The method of the present invention can comprise a further step of vacuum packing the composition and optionally freezing and storing at −20° C.

The present invention further relates to a method of producing a probiotic composition, which comprises cultivating the strain of *S. salivarius*, preferably *S. salivarius* K12, *S. salivarius* ENT-K12, or *S. salivarius* M18, in growth medium which comprises dextrose and yeast extract as carbon, protein and nitrogen source, respectively but which does not comprise a milk product, and in particular no whey permeat, milk or skim milk powder, and preferably also no casein. Preferably, the medium further comprises a buffering agent like di-potassium phosphate, an emulsifier like polysorbate 80, an anti-foaming agent, magnesium sulfate and manganese sulfate. Cultivation is performed preferably at pH 6.8 to 7.2, most preferably at pH 7.1 over the whole course of the cultivation. Otherwise, the cultivation conditions are the same as described above and the further processing of the culture, i.e. concentrating the culture, mixing with lyoprotectants, freeze-drying and optionally milling and homogenizing are performed as described above.

As detailed in Example 4 and explained above, it has been shown that the presence of ascorbate has a stabilizing effect on the *S. salivarius* cells, leading to a more stable composition (represented by the tested CFU amount) in comparison to a composition which has been prepared based on *S. salivarius* cells that have been cultivated in growth medium without ascorbate.

Thus, the present invention also relates to a method of producing a probiotic composition, which comprises cultivation of a *Streptococcus salivarius* strain, preferably *S. salivarius* K12, ENT-K12, M18, or M18DF in growth medium comprising ascorbate and to the use of ascorbate for the cultivation of *S. salivarius* and for producing the corresponding raw material and probiotic composition, respectively.

In a preferred embodiment, the method of the present invention comprises cultivation at 30° C. to 37° C., preferably at 30° C. to 35° C., most preferably at 33° C.

In a preferred embodiment, the method of the present invention comprises cultivation at pH 6.8 to 7.2, preferably at pH 7.1, preferably over the whole course of the cultivation.

In a further preferred embodiment, the method of the present invention comprises cultivation in growth medium comprising a carbon source, preferably dextrose, preferably wherein the initial concentration of the carbon source, in particular dextrose is about 25 g/L to 40 g/L.

Preferably, the method of the present invention comprises cultivation with dissolve oxygen (DO) control and in a preferred embodiment, the DO concentration is kept between 50% and 80% until the carbon source reaches 10 to 15 g/L, and wherein the DO concentration is kept between 0% and 50% in the second half of the cultivation, i.e. when the carbon source concentration drops under 10 to 15 g/L.

The method of the present invention further comprises the concentration of the culture and mixing the concentrate with lyoprotectants, wherein the pH of the mixture is preferably adjusted to about 6.8 to 7.2. Concentration of the culture is preferably performed when the cells reached a desired cell density, after a predetermined time and/or when the carbon source is used up. The method of the present invention further comprises freeze-drying of the mixture to obtain the freeze-dried probiotic composition, wherein freeze-drying is preferably performed for 72 hours. Optionally the mixture is milled and homogenized to a powder.

The growth medium preferably used in the method of the present invention is described above. In particular, in one embodiment, the growth medium comprises dextrose, yeast extract, a milk product, preferably whey permeat, and ascorbate, preferably wherein the growth medium further comprises casein peptone, an emulsifier, preferably polysorbate 80, a buffering agent, preferably di-potassium phosphate and an anti-foaming agent.

In one embodiment, the growth medium comprises yeast extract, dextrose and ascorbate, but no milk products as defined above, preferably wherein the growth medium further comprises a buffering agent, preferably di-potassium phosphate, an emulsifier, preferably polysorbate 80, magnesium sulfate, manganese sulfate, and an anti-foaming agent.

The lyoprotectants as used in the method of the present invention are preferably trehalose, lactitol monohydrate, and maltodextrin; or trehalose, dextrose, sodium ascorbate, sodium citrate and L-cystein.

All of those ingredients are safe for human consumption and can optionally be provided as pharmaceutical grade compounds. Furthermore, the growth medium which comprises no milk products as well as the mixture of lyoprotectants are even free of allergens.

The method of the present invention can comprise a further step of vacuum packing the composition and optionally freezing and storing at −20° C.

The present invention further relates to a composition which is produced by the method of the present invention. Preferably, the composition comprises the *Streptococcus salivarius* strain, preferably *S. salivarius* K12, *S. salivarius* ENT-K12, *S. salivarius* M18, or *S. salivarius* M18DF, maltodextrin, trehalose, lactitol, and moisture; or the composition comprises the *Streptococcus salivarius* strain, preferably *S. salivarius* K12, *S. salivarius* ENT-K12, *S. salivarius* M18, or *S. salivarius* M18DF, trehalose, dextrose, sodium ascorbate, and sodium citrate.

The first composition may further comprise traces of a diary product and/or lactose due to the cultivation of *S. salivarius* in growth medium comprising a milk product, in particular whey. To the contrary, the latter composition does not comprise a milk product and/or lactose, and thus, is allergen-free.

Thus, the present invention provides a composition that is safe for human consumption and a composition which is not only safe for human consumption, but also allergen free.

The present invention further relates to a method of producing a probiotic raw material, wherein the method of the present invention comprises cultivation of a *Streptococcus salivarius* strain, preferably *S. salivarius* K12, *S. salivarius* ENT-K12, *S. salivarius* M18, or *S. salivarius* M18DF, in growth medium comprising dextrose at pH 6.8 to 7.2, preferably at pH 7.1, until the concentration of dextrose reached 10-15 g/L. The method further comprises a step of lowering the pH when the concentration of dextrose reached 10-15 g/L, preferably to 5, and more preferably to 5.1 to 5.5, over 30 min to 3 hours, preferably over 40 minutes to 1 hour, and a step of raising the pH again to a pH value between 6.8 and 7.2 until end of cultivation. End of cultivation is preferably reached as soon as the dextrose is used up, i.e. when the dextrose concentration is about 0 g/L. This pH lowering has the surprising effect that a higher cell-count and more stable cells can be achieved. Without intended to be bound by theory, it is prudent to expect that the pH stress eliminates damaged bacteria which leads to a more stable and viable cell culture.

In a preferred embodiment, the method of the present invention comprises cultivation at 30° C. to 37° C., preferably at 30° C. to 35° C., most preferably at 33° C. In a further preferred embodiment, the method of the present invention comprises cultivation in growth medium having an initial concentration of dextrose of 25 g/L to 40 g/L.

Preferably, the method of the present invention comprises cultivation with dissolve oxygen (DO) control and in a preferred embodiment, the DO concentration is kept between 50% and 80% in the first half of the cultivation, i.e. until the carbon source reaches 10 to 15 g/L and before the pH is lowered, and wherein the DO concentration is kept between 0% and 50% in the second half of the cultivation, i.e. when the carbon source concentration drops under 10 to 15 g/L.

The method of the present invention further comprises harvesting of the *Streptococcus salivarius* strain, i.e. the *Streptococcus salivarius* culture is concentrated.

Since the probiotic raw material is used for human consumption, the raw materials used for the cultivation of *S. salivarius* should be safe for human consumption, for example have to have the GRAS (generally recognized as safe) status. Furthermore, it is preferred that the raw materials for cultivation are not only safe for human consumption, but are also free of allergens and/or are pharmaceutical-grade and GMP grade, respectively.

Thus, in one embodiment, the growth medium used in the method of the present invention comprises yeast extract, casein-peptone, a (further) milk product, preferably whey, and dextrose, preferably wherein the growth medium further comprises an emulsifier like polysorbate 80, a buffering agent like di-potassium phosphate and a de-foaming agent.

In another embodiment, the growth medium used in the method of the present invention comprises yeast extract and dextrose, but no milk products. In particular no whey permeat, milk or skim milk powder is used. The growth medium preferably further comprises a buffering agent like di-potassium phosphate, a de-foaming agent, an emulsifier like polysorbate 80, magnesium sulfate and manganese sulfate.

In one embodiment, the growth medium used in the method of the present invention further comprises ascorbate.

In particular, in one embodiment, the growth medium comprises dextrose, yeast extract, a milk product, preferably whey permeat, and ascorbate, preferably wherein the growth medium further comprises casein peptone, an emulsifier, preferably polysorbate 80, a buffering agent, preferably di-potassium phosphate and an anti-foaming agent.

In one embodiment, the growth medium comprises yeast extract, dextrose and ascorbate, but no milk products as defined above, preferably wherein the growth medium further comprises a buffering agent, preferably di-potassium phosphate, an emulsifier, preferably polysorbate 80, magnesium sulfate, manganese sulfate, and an anti-foaming agent.

All of those ingredients are safe for human consumption, can be optionally provided as pharmaceutical grade compounds, and the growth medium which comprises no milk products is even free of allergens.

The present invention further relates to a method of producing a probiotic raw material, which comprises cultivating the strain of *S. salivarius*, preferably *S. salivarius* K12, *S. salivarius* ENT-K12, *S. salivarius* M18, or *S. salivarius* M18DF, in growth medium which comprises dextrose and yeast extract as carbon, protein and nitrogen source, respectively but which does not comprise a milk product, and in particular no whey permeat, milk, and skim milk powder. Preferably, the medium does not comprise casein. In a one embodiment, the growth medium further comprises ascorbate. Preferably, the medium further comprises a buffering agent, preferably di-potassium phosphate, a de-foaming agent, an emulsifier, preferably polysorbate 80, magnesium sulfate and manganese sulfate. Cultivation is performed preferably at pH 6.8 to 7.2, most preferably at pH 7.1 over the whole course of the cultivation. Otherwise, the cultivation conditions are the same as described above and the further processing of the culture, i.e. the harvesting is performed as described above.

As detailed in Example 4 and explained above, it has been shown that the presence of ascorbate has a stabilizing effect on the *S. salivarius* cells, leading to a more stable composition (represented by the tested CFU amount) in comparison to a composition which has been prepared based on *S. salivarius* cells that have been cultivated in growth medium without ascorbate.

Thus, the present invention also relates to a method of producing a probiotic raw material, which comprises cultivation of a *Streptococcus salivarius* strain, preferably *S. salivarius* K12, ENT-K12, M18, or M18DF in growth medium comprising ascorbate.

In a preferred embodiment, the method of the present invention comprises cultivation at 30° C. to 37° C., preferably at 30° C. to 35° C., most preferably at 33° C.

In a preferred embodiment, the method of the present invention comprises cultivation at pH 6.8 to 7.2, preferably at pH 7.1.

In a further preferred embodiment, the method of the present invention comprises cultivation in growth medium comprising a carbon source, preferably with dextrose as carbon source, preferably wherein the initial concentration of the carbon source, in particular dextrose is about 25 g/L to 40 g/L.

Preferably, the method of the present invention comprises cultivation with dissolve oxygen (DO) control and in a preferred embodiment, the DO concentration is kept between 50% and 80% until the carbon source reaches 10 to 15 g/L, and wherein the DO concentration is kept between 0% and 50% in the second half of the cultivation, i.e. when the carbon source concentration drops under 10 to 15 g/L.

The growth medium used in the method of the present invention is described above. In particular, in one embodiment, the growth medium comprises dextrose, yeast extract, a milk product, preferably whey permeat, and ascorbate, preferably wherein the growth medium further comprises casein peptone, an emulsifier, preferably polysorbate 80, a buffering agent, preferably di-potassium phosphate and an anti-foaming agent.

In one embodiment, the growth medium comprises yeast extract, dextrose and ascorbate, but no milk products as defined above, preferably wherein the growth medium further comprises a buffering agent, preferably di-potassium phosphate, an emulsifier, preferably polysorbate 80, magnesium sulfate, manganese sulfate, and an anti-foaming agent.

All of those ingredients are safe for human consumption, can be optionally provided as pharmaceutical grade compounds, and the growth medium which comprises no milk products is even free of allergens. The further processing of the culture, i.e. the harvesting is performed as described above.

The present invention further relates to a probiotic raw material which is produced by the method of the present invention, wherein in one embodiment, the raw material may further comprise traces of diary products and/or lactose due to the cultivation of *S. salivarius* in growth medium comprising a milk product, in particular whey. In another embodiment, the raw material does not comprise a milk product and/or lactose since cultivation has been performed in growth medium without a milk product, and thus, the raw material is allergen-free. Thus, the present invention provides a raw material that is safe for human consumption and a raw material which is also allergen free. Particularly preferred, the probiotic raw material comprises *S. salivarius* K12, also designated ENT-K12® for the allergen-free product.

The invention further relates to the use of the composition and the raw material, respectively for producing probiotic and pharmaceutical products, preferably tablets, in particular lozenges or a chewable tablets, chewing gums, capsules, sachets, foods, drinks, confectionaries, or nutraceuticals.

The present invention also provides a method of cultivating *S. salivarius*, in particular *S. salivarius* K12, *S. salivarius* ENT-K12, *S. salivarius* M18, or *S. salivarius* M18DF.

The method of the present invention for cultivating the *S. salivarius* strain is performed in growth medium comprising dextrose at pH 6.8 to 7.2, preferably at pH 7.1, until the concentration of dextrose reached 10-15 g/L. The method further comprises a step of lowering the pH over 30 min to 3 hours when the concentration of dextrose reached 10-15 g/L, and a step of raising the pH again to a pH value between 6.8 and 7.2 until end of cultivation. End of cultivation is preferably reached as soon as the dextrose is used up, i.e. when the dextrose concentration is about 0 g/L.

In a preferred embodiment, the method of the present invention comprises cultivation at 30° C. to 37° C., preferably at 30° C. to 35° C., most preferably at 33° C. In a further preferred embodiment, the method of the present invention comprises cultivation in growth medium having an initial concentration of dextrose of 25 to 40 g/L.

Preferably, the method of the present invention comprises cultivation with dissolve oxygen (DO) control and in a preferred embodiment, the DO concentration is kept between 50% and 80% in the first half of the cultivation, i.e. until the carbon source reaches 10 to 15 g/L and before the pH is lowered, and wherein the DO concentration is kept between 0% and 50% in the second half of the cultivation, i.e. when the carbon source concentration drops under 10 to 15 g/L.

In one embodiment, the growth medium comprises yeast extract, a milk product, preferably whey, and dextrose, preferably wherein the growth medium further comprises an emulsifier like polysorbate 80, a buffering agent like di-potassium phosphate, and a de-foaming agent. Furthermore, casein peptone may be comprised in the growth medium.

In another embodiment, the growth medium comprises yeast extract and dextrose, but no milk products. In particular no whey permeat, milk or skim milk powder is used. Preferably, also no casein is present in the growth medium. The growth medium preferably further comprises a buffering agent like di-potassium phosphate, a de-foaming agent, an emulsifier like polysorbate 80, magnesium sulfate and manganese sulfate.

In one embodiment, the growth medium used in the method of the present invention further comprises ascorbate.

In particular, in one embodiment, the growth medium comprises dextrose, yeast extract, a milk product, preferably whey permeat, and ascorbate, preferably wherein the growth medium further comprises casein peptone, an emulsifier, preferably polysorbate 80, a buffering agent, preferably di-potassium phosphate and an anti-foaming agent.

In one embodiment, the growth medium comprises yeast extract, dextrose and ascorbate, but no milk products as defined above, preferably wherein the growth medium further comprises a buffering agent, preferably di-potassium phosphate, an emulsifier, preferably polysorbate 80, magnesium sulfate, manganese sulfate, and an anti-foaming agent.

The present invention further relates to a method of cultivating the strain of *S. salivarius*, preferably *S. salivarius* K12, *S. salivarius* ENT-K12, *S. salivarius* M18, or *S. salivarius* M18DF, in growth medium which comprises dextrose and yeast extract as carbon, protein and nitrogen source, respectively but which does not comprise a milk product, and in particular no whey permeat, milk or skim milk powder. Preferably, also no casein is present in the growth medium. In a one embodiment, the growth medium further comprises ascorbate. Preferably, the medium further comprises a buffering agent like di-potassium phosphate, a de-foaming agent, an emulsifier like polysorbate 80, magnesium sulfate and manganese sulfate. Cultivation is performed preferably at pH 6.8 to 7.2, most preferably at pH 7.1 over the whole course of the cultivation. Otherwise, the cultivation conditions are the same as described above.

As detailed in Example 4 and explained above, it has been shown that the presence of ascorbate has a stabilizing effect on the *S. salivarius* cells, leading to a more stable composition (represented by the tested CFU amount) in comparison to a composition which has been prepared based on *S. salivarius* cells that have been cultivated in growth medium without ascorbate.

Thus, the present invention also relates to a method of cultivating *Streptococcus salivarius*, preferably *S. salivarius* K12, ENT-K12, M18, or M18DF in growth medium comprising ascorbate.

In a preferred embodiment, the method of the present invention comprises cultivation at 30° C. to 37° C., preferably at 30° C. to 35° C., most preferably at 33° C.

In a preferred embodiment, the method of the present invention comprises cultivation at pH 6.8 to 7.2, preferably at pH 7.1.

In a further preferred embodiment, the method of the present invention comprises cultivation in growth medium comprising a carbon source, preferably with dextrose as carbon source, preferably wherein the initial concentration of the carbon source, in particular dextrose is about 25 g/L to 40 g/L.

Preferably, the method of the present invention comprises cultivation with dissolve oxygen (DO) control and in a preferred embodiment, the DO concentration is kept between 50% and 80% until the carbon source reaches 10 to 15 g/L, and wherein the DO concentration is kept between 0% and 50% in the second half of the cultivation, i.e. when the carbon source concentration drops under 10 to 15 g/L.

The growth medium used in the method of the present invention is described above. In particular, in one embodiment, the growth medium comprises dextrose, yeast extract, a milk product, preferably whey permeat, and ascorbate, preferably wherein the growth medium further comprises casein peptone, an emulsifier, preferably polysorbate 80, a buffering agent, preferably di-potassium phosphate and an anti-foaming agent.

In one embodiment, the growth medium comprises yeast extract, dextrose and ascorbate, but no milk products as defined above, preferably wherein the growth medium further comprises a buffering agent, preferably di-potassium phosphate, an emulsifier, preferably polysorbate 80, magnesium sulfate, manganese sulfate, and an anti-foaming agent.

All of those ingredients are safe for human consumption, can be optionally provided as pharmaceutical grade compounds, and the growth medium which comprises no milk products is even free of allergens.

As mentioned above, using an allergen-free medium for cultivation of *S. salivarius* is of particular importance for consumer consumption. Accordingly, the present invention also relates to the use of an allergen-free medium for the cultivation of *Streptococcus salivarius*, preferably *S. salivarius* K12, ENT-K12, M18, or M18DF, and for producing the corresponding raw material, and for producing a probiotic composition comprising *S. salivarius*, respectively. Preferably, the growth medium comprises yeast extract and dextrose, but no milk products. In particular no whey permeat, milk skim milk powder or casein-peptone is used. In one embodiment, the growth medium preferably further comprises a buffering agent, preferably di-potassium phosphate, an emulsifier, preferably polysorbate 80, magnesium sulfate, manganese sulfate, and an anti-foaming agent. In another embodiment, the growth medium preferably further comprises ascorbate, a buffering agent, preferably di-potassium phosphate, an emulsifier, preferably polysorbate 80, magnesium sulfate, manganese sulfate, and an anti-foaming agent.

Further embodiments of the present invention will be apparent from the description, the Figures and Examples that follow.

DETAILED DESCRIPTION OF THE INVENTION

Figure 1:
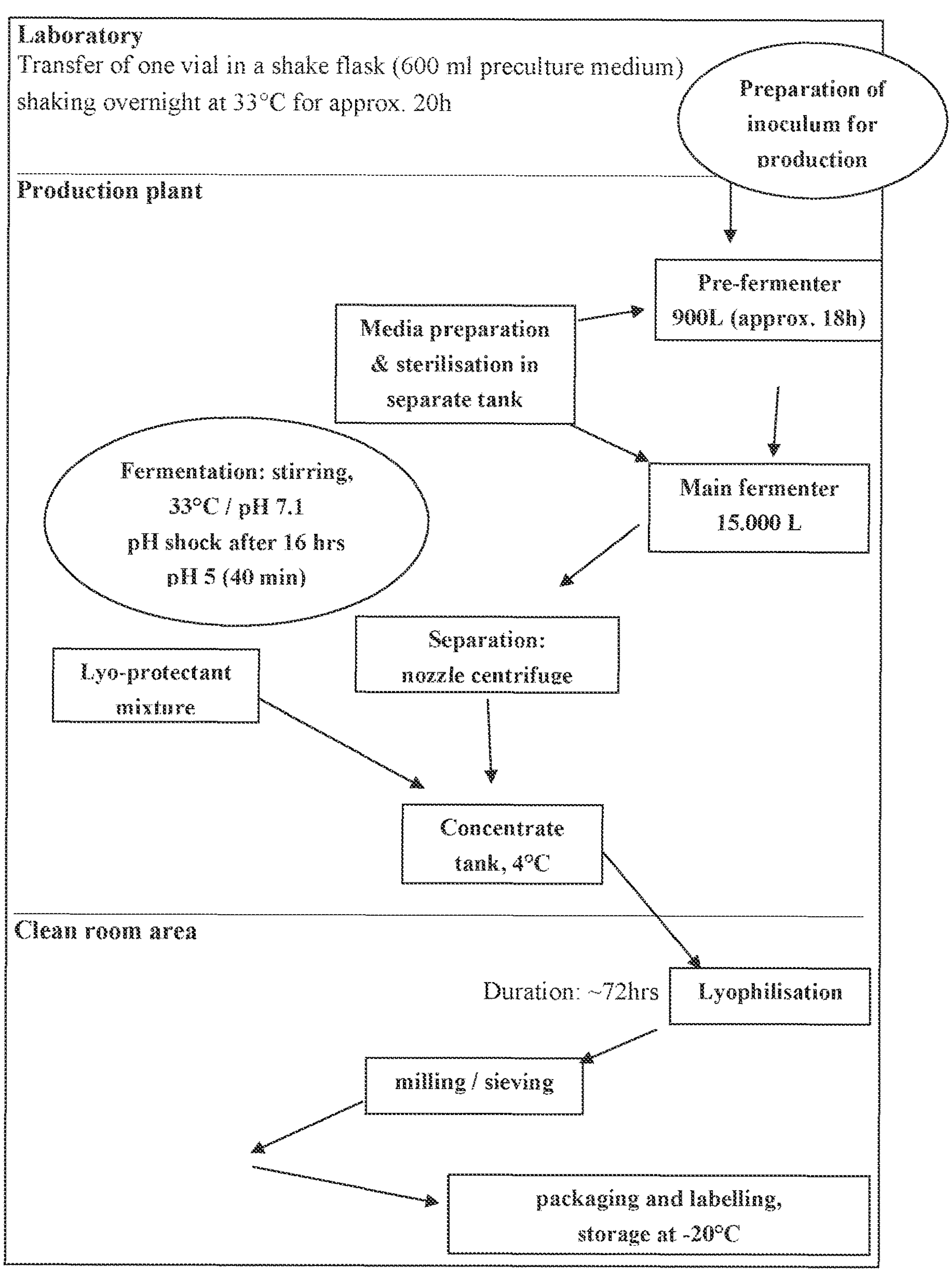
FIG. 1: Flowchart for the manufacturing process of a probiotic composition comprising a *Streptococcus salivarius* strain which includes cultivation in medium comprising dextrose, yeast extract, casein-peptone, di-potassium phosphate, polysorbate 80 and whey permeat.

The present invention relates to a method of producing a probiotic composition, which involves culturing of a *Streptococcus salivarius* strain. Preferably, the strain is *S. salivarius* K12, which is publicly available at the American Type Culture Collection (ATCC), P.O. Box 1549, Manassas, VA 20108, USA under Accession No. BAA-1024, or *S. salivarius* ENT-K12, which is genetically identical to *S. salivarius* K12 and has been deposited at the Leibniz-Institut DSMZ—Deutsche Sammlung von Mikroorganismen und Zellkulturen GmbH, Inhoffenstraße 7B, 38124 Braunschweig, Germany, and assigned Accession Number DSM 34540. As evidenced by the GRAS Notice (GRN) No. 807 and the GRAS Notice (GRN) No. 591 of the FDA, *S. salivarius* M18 exhibits same growth characteristics than *S. salivarius* K12 and same culture conditions can be used for cultivation of both strains. Thus, the method of the present invention involves in one embodiment the cultivation of *S. salivarius* M18, which is publicly available at the ATCC under Accession No. BAA-2593, or *S. salivarius* M18DF, which is genetically identical to *S. salivarius* M18, has been deposited at the Leibniz-Institut DSMZ—Deutsche Sammlung von Mikroorganismen und Zellkulturen GmbH, Inhoffenstraße 7B, 38124 Braunschweig, Germany, and assigned Accession Number DSM 34886.

Accordingly, when reference is made to a *S. salivarius* strain, in general every *S. salivarius* strain is meant, but preferably *S. salivarius* K12, *S. salivarius* ENT-K12, *S. salivarius* M18, or *S. salivarius* M18DF, and most preferably *S. salivarius* K12 or *S. salivarius* ENT-K12.

The present invention relates in particular to a method of producing a freeze-dried probiotic composition, which is preferably in powder form, wherein the method comprises the cultivation of the *S. salivarius* strain, wherein a pH lowering is performed during the cultivation. This is particularly advantageous since the pH lowering results in higher cell-count and/or more stable cells. The pH lowering can be performed for a time sufficient to have a stable pH.

In particular, the strain is cultivated in growth medium with controlled pH and controlled temperature. In particular, the pH is adjusted to a pH value of about 7, in particular to a pH value of 6.8 to 7.2, preferably to pH 7.1 until the pH lowering is performed. During the pH lowering, the pH value is set to about 5, in particular to 5.1 to 5.5, and after a certain time, which can vary between 30 minutes and 3 hours, but which is preferably between 40 minutes and 1 hour, and most preferably 40 minutes, the pH is raised again to a value of about 6.8 to 7.2. The decrease of the pH value can be performed with various pH lowering agents like phosphoric acid ($H_3PO_4$), lactic acid or hydrochloric acid (HCl), but preferably lactic acid is used.

The cultivation is performed in growth medium comprising dextrose, wherein the pH lowering is initiated, i.e. the pH is lowered from a value of 6.8 to 7.2 to a value of about 5, in particular to a value between pH 5.1 and 5.5, when the dextrose concentration reached about 10 to 15 g/L. Dependent on the growth medium used, the pH lowering is initiated at about 8 to 16 hours after start of the cultivation. Thus, the dextrose concentration at the beginning of the cultivation certainly has to be higher than 10 to 15 g/L and is preferably about 25 to 40 g/L.

As mentioned above, after lowering the pH, the pH is raised again after a certain time to 6.8 to 7.2 and is kept constant until end of the cultivation. End of the cultivation is reached when the dextrose is used up, i.e. when the dextrose concentration is about 0 g/L.

*S. salivarius* is a mesophilic species and those grow best in moderate temperature, with an optimum growth range from 20 to 45° C. Preferably, the *S. salivarius* strain is grown at 30° C. to 37° C., even more preferred at 30° C. to 35° C., most preferred at 33° C.

Preferably, cultivation is also performed with dissolve oxygen (DO) control and in a preferred embodiment of the present invention, the DO concentration is kept between 50% and 80% in the first half of the cultivation, i.e. until the carbon source reaches 10 to 15 g/L and before the pH is lowered, and wherein the DO concentration is kept between 0% and 50% in the second half of the cultivation, i.e. when the carbon source concentration drops under 10 to 15 g/L.

The present invention also relates to a method of producing a freeze-dried probiotic composition, which is preferably in powder form, wherein the method comprises the cultivation of the *S. salivarius* strain, wherein a growth medium comprising ascorbate is used during the cultivation. This is particularly advantageous since the presence of ascorbate results in more stable cells, as represented for example by the higher CFU count as shown in Example 4.

In a preferred embodiment, the method of the present invention comprises cultivation at 30° C. to 37° C., preferably at 30° C. to 35° C., most preferably at 33° C.

In a preferred embodiment, the method of the present invention comprises cultivation at pH 6.8 to 7.2, preferably at pH 7.1.

In a further preferred embodiment, the method of the present invention comprises cultivation in growth medium comprising a carbon source, preferably with dextrose as carbon source, preferably wherein the initial concentration of the carbon source, in particular dextrose is about 25 g/L to 40 g/L.

Preferably, the method of the present invention comprises cultivation with dissolve oxygen (DO) control and in a preferred embodiment, the DO concentration is kept between 50% and 80% until the carbon source reaches 10 to 15 g/L, and wherein the DO concentration is kept between 0% and 50% in the second half of the cultivation, i.e. when the carbon source concentration drops under 10 to 15 g/L.

Cultivation of *S. salivarius* is performed in a bioreactor, and is preferably performed in a large scale bioreactor having a volume of 15.000 liter for producing *S. salivarius* for propiotic/food products. Pharmaceutical grade production is preferably performed in a small biotector, for example having a volume of about 1.000 liter. Accordingly, a pre-cultivation has to be performed and a pre-fermenter has to be run in order to produce an inoculum for inoculating the main bioreactor.

Thus, in one embodiment of the present invention, the above-described main cultivation of the *S. salivarius* strain is preceded by the following steps:

A pre-culture is prepared by transferring the strain into about 600 ml of the growth medium, preferably at a optical density of 2-4, and cultivation is performed for about 20 to 24 hours in a shake flask or grow bottle at 30° C. to 37° C., preferably at 30° C. to 35° C., and most preferably at 33° C. In a preferred embodiment, the strain was frozen before and was thawed before inoculation. Afterwards, a seed culture is prepared by transferring the pre-culture into a fermentation vessel, i.e. a bioreactor and cultivation is performed for about 14 hours to 18 hours and/or until an optical density (OD) of the culture of about 1.5 to 3 is reached. The seed culture for the 15.000 liter fermenter is prepared by transferring the pre-culture into 900 L of the growth medium and cultivation is performed in a fermentation vessel, i.e. a bioreactor for about 14 hours to 18 hours and/or until an optical density (OD) of the culture of about 1.5 to 3 is reached.

The cultivation is pH and temperature controlled and cultivation is preferably performed at 30° C. to 37° C. and pH 6.8 to 7.2, preferably at 30° C. to 35° C., most preferably at 33° C. and/or pH 7.1 or 7.2. The next step comprises the transfer of the whole seed culture to the main culture and cultivation is performed as described above in connection with the method of the present invention.

The growth medium used in the method of the present invention comprises at least dextrose as carbon source. All ingredients for the growth medium and processing aids are food grade standard and/or pharmaceutical grade (GMP-grade), GMO-free, free of BSE/TSE and meet Halal requirements.

The safety of strain K12, and thus of ENT-K12, M18, and M18DF has been specifically supported by a series of studies: affirming the absence of known streptococcal virulence factors and antibiotic resistance determinants; showing its low mutagenicity predisposition; acute and subacute toxicity testing in rats; and a high-dosage trial in humans. The outcome of these strain-specific studies, together with recognition of the inherent safety of the species, has classified *S. salivarius* K12 and M18 as a "generally recognized as safe" (or "GRAS") organism in the USA and as a risk group 1 organism in Germany by the Ausschuß für Biologische Arbeitsstoffe (Translation: Committee on Biological Agents); see Wescombe et al. Developing oral probiotics from *Streptococcus salivarius*, Future Microbiol. 7 (2012), 1355-71 as well as references cited therein and the GRAS Notices No. 807 and No. 591 of the FDA.

In one embodiment, the growth medium used in the method of the present invention comprises next to dextrose, at least yeast extract and a milk product. The milk product can be for example skim milk powder, whey permeat, or milk, but preferably whey permeat is used. In a preferred embodiment, the growth medium further comprises a protein source, preferably casein-peptone. More preferably, the medium further comprises a buffering agent. Buffers can be for example phosphate, citrate or acetate buffers, wherein preferably di-potassium phosphate is used as buffering agent. However, further suitable buffers are known to the person skilled in the art. More preferably, the medium further comprises an emulsifier. Emulsifiers are known to the person skilled in the art and comprise for example lecithin (egg or soy lecithin), hypromelose or polysorbate, in particular polysorbate 80. Preferably, polysorbate 80 is comprised in the fermentation medium. Moreover, a de-foaming agent can be comprised in the medium. De-foaming agents or anti-foaming agents are known to the persion skilled in the art and comprise for example polyethylenglycol, silicon, or fatty acid esters. The medium ingredients are dissolved in water. Furthermore, additional processing aids, in particular for adjusting the pH during cultivation, are used like ammonia solution (25%), sodium hydroxide (30%), hydrochloride acid (33.8%), phosphoric acid and/or lactic acid.

In one embodiment, the growth medium further comprises ascorbate.

In a preferred embodiment, the growth medium comprises or essentially consists of yeast extract, di-potassium phosphate, dextrose monohydrate, whey permeat, casein peptone, polysorbate 80 and optionally defoaming agent, in particular 3-8 g/l yeast extract, 1.5-2.2 g/l di-potassium phosphate, 7-12 g/l dextrose monohydrate, 24-28 g/l whey permeate, 15-20 g/l casein-peptone and 0.5-1.0 g/l polysorbate 80, and 0.1 g/l of a de-foaming agent.

In a further preferred embodiment, the growth medium comprises or essentially consists of yeast extract, di-potassium phosphate, dextrose monohydrate, whey permeat, casein peptone, polysorbate 80, ascorbate and optionally defoaming agent, in particular 3-8 g/l yeast extract, 1.5-2.2 g/l di-potassium phosphate, 7-12 g/l dextrose monohydrate, 24-28 g/l whey permeate, 15-20 g/l casein-peptone, 0.5-1.0 g/l polysorbate 80, and 0.1-1.0 g/l, preferably 0.1-0.5 g/l ascorbate, and 0.1 g/l of a de-foaming agent.

In another embodiment, the growth medium used in the method of the present invention comprises next to dextrose, yeast extract, but no milk products. In particular no whey permeat, milk or skim milk powder are used in the growth medium and/or no casein. The growth medium preferably further comprises a buffering agent. Buffers can be for example phosphate, citrate or acetate buffers, wherein preferably di-potassium phosphate is used as buffering agent. However, further suitable buffers are known to the person skilled in the art. More preferably, the medium further comprises an emulsifier. Emulsifiers are known to the person skilled in the art and comprise for example lecithin (egg or soy lecithin), hypromelose or polysorbate, in particular polysorbate 80. Preferably, polysorbate 80 is comprised in the fermentation medium. In one preferred embodiment, the medium comprises manganese sulfate and magnesium sulfate. Moreover, a de-foaming agent can be comprised in the medium. De-foaming agents or anti-foaming agents are known to the persion skilled in the art and comprise for example polyethylenglycol, silicon, or fatty acid esters. The medium ingredients are dissolved in water. Furthermore, additional processing aids, in particular for adjusting the pH during cultivation, are used like ammonia solution (25%), sodium hydroxide (30%), hydrochloride acid (33.8%), phosphoric acid and/or lactic acid, but in particular ammonia solution (25%) and phosphoric acid. Such a growth medium has not only food grade standard and/or pharmaceutical grade, is GMO-free, free of BSE/TSE and meets Halal requirements, but is also allergen free according to EU Regulation 1169/2011.

In one embodiment, the growth medium further comprises ascorbate.

In a preferred embodiment, the growth medium comprises or essentially consists of yeast extract, dextrose monohydrate, di-potassium phosphate, polysorbate 80, manganese sulfate, magnesium sulfate, and optionally a de-foaming agent, and in particular 17-25 g/l yeast extract, 1.5-2 g/l di-potassium phosphate, 0.02-0.1 g/l manganese sulfate, 0.1 g/l of a de-foaming agent, 0.5-1 g/l polysorbate 80, 25-40 g/l dextrose monohydrate, and 0.2-0.4 g/l magnesium sulfate, which are dissolved in water.

In a further preferred embodiment, the growth medium comprises or essentially consists of yeast extract, dextrose monohydrate, di-potassium phosphate, polysorbate 80, manganese sulfate, magnesium sulfate, ascorbate, and optionally a de-foaming agent, and in particular 17-25 g/l yeast extract, 1.5-2 g/l di-potassium phosphate, 0.02-0.1 g/l manganese sulfate, 0.1 g/l of a de-foaming agent, 0.5-1 g/l polysorbate 80, 25-40 g/l dextrose monohydrate, 0.1-1.0 g/l, preferably 0.1-0.5 g/l ascorbate, and 0.2-0.4 g/l magnesium sulfate, which are dissolved in water.

At the end of the cultivation, e.g. when the dextrose is used up or when the desired cell density is reached, the culture is harvested, i.e. concentrated. This can be performed by various methods known to the skilled person like filtration and centrifugation. The harvesting is preferably performed by centrifugally concentrating the culture using a separator.

In order to improve long-term stability of the probiotic composition, freeze-drying in the presence of lyoprotectants is performed. Thus, the concentrated culture is mixed with lyoprotectants. A lyoprotectant is any substance added to something undergoing lyophilization in order to prevent damage, is chemically inert and does not react with the lyophilized product. Lyoprotectants can be diverse and are for example sugars, sugar alcohols, polymers and other buffering substances like glucose, trehalose, sucrose, maltose, maltodextrin, lactitol monohydrate, lactose, mannitol, inositol, hydroxypropyl-β-cyclodextrin, polyethylene glycol, sodium ascorbate and sodium citrate. Those can be either used alone or in combination.

In a preferred embodiment, not only the ingredients of the growth medium and the processing aids are food grade standard, and/or pharmaceutical grade (GMP-grade), GMO-free, free of BSE/TSE, meet Halal requirements, and are optionally hypo allergen, but the lyoprotectants are allergen free according to EU Regulation 1169/2011 as well.

The lyoprotectants as used in the method of the present invention are preferably (i) one, two or preferably all three selected from trehalose, lactitol monohydrate, and maltodextrin; or (ii) one, two, three, four, or preferably all five selected from trehalose, dextrose, sodium ascorbate, sodium citrate and L-cystein. Preferably, the latter mix of lyoprotectants is used in the method of the present invention, wherein cultivation of *S. salivarius* is performed in medium without any milk products, i.e. in allergen-free medium.

In a preferred embodiment, the mix of lyoprotectants as used in the method of the present invention comprises (i) trehalose in a concentration of 1-2 g/L fermentation broth, lactitol monohydrate in a concentration of 0.5-1 g/L fermentation broth, and maltodextrin in a concentration of 3-4 g/L fermentation broth; or (iii) trehalose in a concentration of 4-7 g/L fermentation broth, dextrose in a concentration of 0.1-0.4 g/L fermentation broth, sodium ascorbate in a concentration of 0.1-0.4 g/L fermentation broth, sodium citrate in a concentration of 0.2-0.6 g/L fermentation broth.

The pH of mixture of the concentrated bacterial culture and the lyoprotectants is preferably adjusted to 6.8 to 7.5 and preferably, sodium hydroxide is used for pH adjustment.

After addition of the lyoprotectants, the mixture is freeze-dried. Optionally the freeze dried product is milled and homogenized to obtain a powder, wherein homogenization is preferably performed with maltodextrin. The method of the present invention optionally further comprises the vacuum packing of the freeze-dried powder, which is stored afterwards at −20° C.

Figure 2:
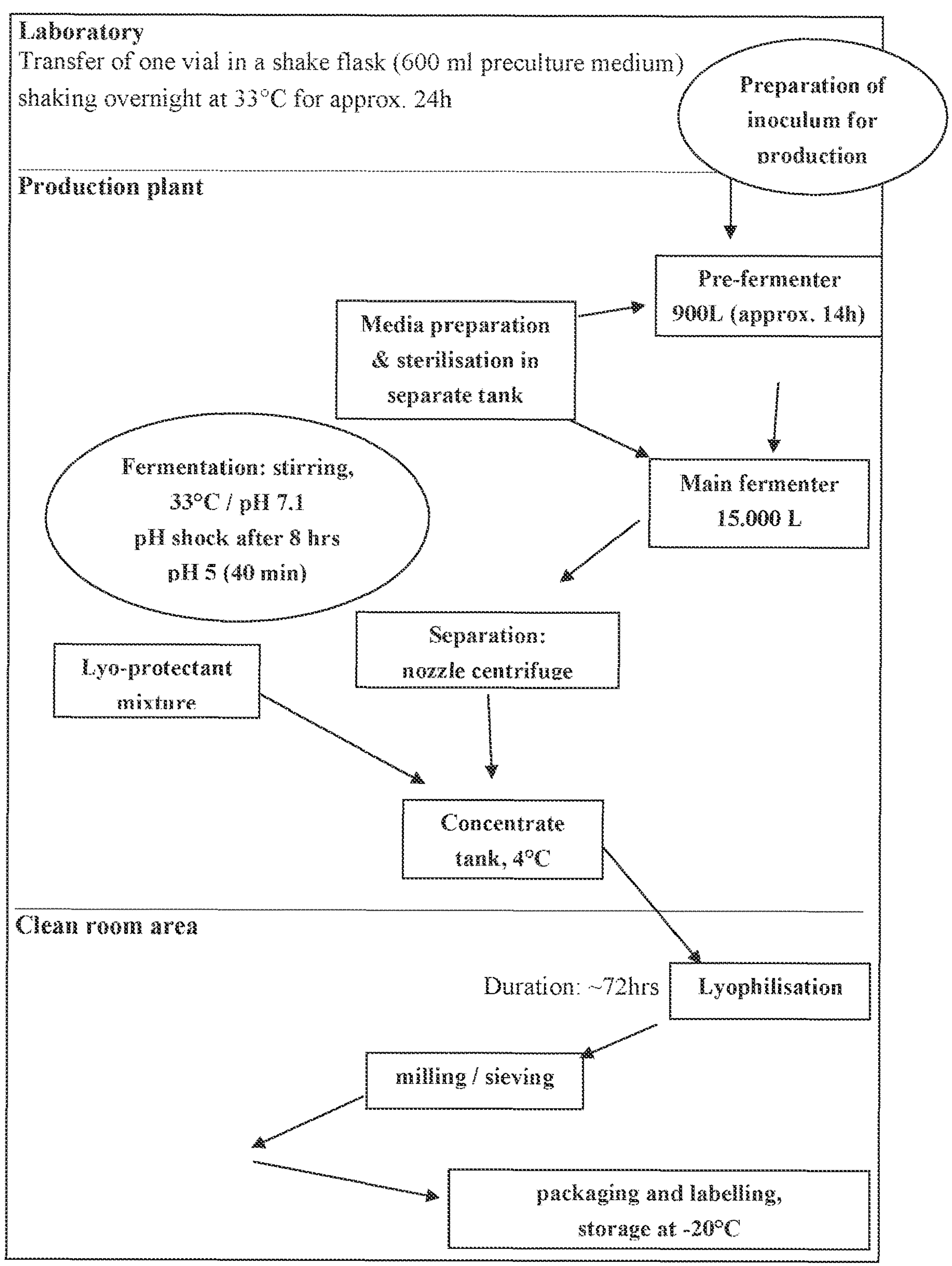
FIG. 2: Flowchart for the manufacturing process of a probiotic composition comprising a *Streptococcus salivarius* strain which includes cultivation in medium comprising dextrose, yeast extract, di-potassium phosphate, polysorbate 80, magnesium sulfate and manganese sulfate.

An overview of the manufacturing process is given in FIG. 1 and FIG. 2.

As mentioned above, the avoidance of a milk product during cultivation of the *S. salivarius* strain is particularly advantage since it produces an allergen-free composition. Accordingly, the present invention further relates to a method of producing a probiotic composition, which comprises cultivating the strain of *S. salivarius*, preferably *S. salivarius* K12, *S. salivarius* ENT-K12, *S. salivarius* M18, or *S. salivarius* M18DF, in growth medium which comprises dextrose and yeast extract as carbon, protein and nitrogen source, respectively but which does not comprise a milk product, and in particular no whey permeat, milk or skim milk powder. Furthermore, the medium preferably does not comprise casein. Preferably, the medium further comprises a buffering agent, preferably di-potassium phosphate, a de-foaming agent, an emulsifier, preferably polysorbate 80, manganese sulfate and magnesium sulfate. In one embodiment, the growth medium further comprises ascorbate. Cultivation is performed preferably at pH 6.8 to 7.2, most preferably at pH 7.1 over the whole course of the cultivation. Otherwise, the cultivation conditions are the same as described above and the further processing of the culture, i.e. concentrating the culture, mixing with lyoprotectants, freeze-drying and optionally milling and homogenizing are also performed as described above.

The present invention further relates to a probiotic composition which comprises the probiotic strain of *Streptococcus salivarius*, maltodextrin, trehalose, lactitol, and moisture. In particular, the composition comprises 25-35% *Streptococcus salivarius*, preferably *S. salivarius* K12, *S. salivarius* ENT-K12, *S. salivarius* M18, or *S. salivarius* M18DF, 40-50% maltodextrin, 10% trehalose, 5% lactitol, and 2-5% moisture. This composition is preferably produced by the method of the present invention, wherein the growth medium preferably comprises dextrose, yeast extract, casein-peptone, di-potassium phosphate, a milk product, preferably whey permeat, polysorbate 80 and an anti-foaming agent; and wherein the lyoprotectants comprise trehalose, lactitol monohydrate, and maltodextrin. This composition is safe for human consumption is comprises nearly no allergens, except milk and milk products, due to the use of the milk product, in particular whey permeat during cultivation; see Table 1.

The present invention further relates to a probiotic composition which comprises the probiotic strain of *Streptococcus salivarius*, trehalose, dextrose, sodium ascorbate and sodium citrate. In particular, the composition comprises 32-40% *Streptococcus salivarius*, preferably *S. salivarius* K12, *S. salivarius* ENT-K12, *S. salivarius* M18, or *S. salivarius* M18DF, 2-3% dextrose, 50-60% trehalose, 2-3% sodium ascorbate, 2-3% sodium citrate, and 2-5% moisture. This composition is preferably produced by the method of the present invention, wherein the growth medium comprises dextrose and yeast extract as carbon, protein and nitrogen source, respectively (but no milk product); and wherein the lyoprotectants comprise trehalose, dextrose, sodium ascorbate sodium citrate and L-cystein. This composition is safe for human consumption and is allergen-free; see Table 2.

TABLE 1

Allergen content of the freeze-dried powder composition, wherein *S. salivarius* is cultivated in growth medium comprising dextrose, yeast extract, and whey permeat as carbon nitrogen and protein source, respectively; and wherein the lyoprotectants comprise trehalose, lactitol monohydrate, and maltodextrin.

| Nr. | ALLERGENS[1] | PRESENT | ABSENT |
|---|---|---|---|
| 1 | Cereals containing gluten namely wheat (such as spelt and Khorasan/Kamut), rye, barley, oats, and their hybridized strains and products thereof[2] | | x |
| 2 | Crustaceans and products thereof | | x |
| 3 | Eggs and products thereof | | x |
| 4 | Fish and products thereof | | x |
| 5 | Peanuts and products thereof | | x |
| 6 | Soybeans and products thereof | | x |
| 7 | Milk and products thereof (including lactose) | x | |
| 8 | Nuts i.e. almonds (*Amygdalus communis* L.), hazelnuts (*Corylus avellana*), walnuts (*Juglans regia*), cashews (*Anacardium occidentale*), pecan nuts (*Carya illinoinensis* (Wangenh.) K. Koch), Brazil nuts (*Bertholletia excelsa*), pistachio nuts (*Pistacia vera*), macadamia or Queensland nuts (*Macadamia ternifolia*) and products thereof | | x |
| 9 | Celery and products thereof | | x |
| 10 | Mustard and products thereof | | x |
| 11 | Sesame seeds and products thereof | | x |
| 12 | Sulphur dioxide and sulphites at concentrations of more than 10 mg/kg or 10 mg/litre in terms of the total $SO_2$ | | x |
| 13 | Lupin and products thereof | | x |
| 14 | Molluscs and products thereof | | x |
| 15 | Bovine and products thereof | | x |
| 16 | Porcine and products thereof | | x |
| 17 | Peach and products thereof | | x |
| 18 | Buckwheat and products thereof | | x |

[1]The allergens list is based on EU regulation no 1169/2011,

[2]Gluten NMT 20 mg/kg

TABLE 2

Allergen content of the freeze-dried powder composition, wherein *S. salivarius* is cultivated in growth medium comprising dextrose and yeast extract as carbon, protein and nitrogen source, respectively (but no milk product); and wherein the lyoprotectants comprise trehalose, dextrose, sodium ascorbate, sodium citrate and L-cystein.

| Nr. | ALLERGENS[1] | PRESENT | ABSENT |
|---|---|---|---|
| 1 | Cereals containing gluten namely wheat (such as spelt and Khorasan/Kamut), rye, barley, oats, and their hybridized strains and products thereof[2] | | x |
| 2 | Crustaceans and products thereof | | x |
| 3 | Eggs and products thereof | | x |
| 4 | Fish and products thereof | | x |
| 5 | Peanuts and products thereof | | x |
| 6 | Soybeans and products thereof | | x |
| 7 | Milk and products thereof (including lactose) | | x |
| 8 | Nuts i.e. almonds (*Amygdalus communis* L.), hazelnuts (*Corylus avellana*), walnuts (*Juglans regia*), cashews (*Anacardium occidentale*), pecan nuts (*Carya illinoinensis* (Wangenh.) K. Koch), Brazil nuts (*Bertholletia excelsa*), pistachio nuts (*Pistacia vera*), macadamia or Queensland nuts (*Macadamia ternifolia*) and products thereof | | x |
| 9 | Celery and products thereof | | x |
| 10 | Mustard and products thereof | | x |
| 11 | Sesame seeds and products thereof | | x |
| 12 | Sulphur dioxide and sulphites at concentrations of more than 10 mg/kg or 10 mg/litre in terms of the total $SO_2$ | | x |
| 13 | Lupin and products thereof | | x |
| 14 | Molluscs and products thereof | | x |
| 15 | Bovine and products thereof | | x |
| 16 | Porcine and products thereof | | x |
| 17 | Peach and products thereof | | x |
| 18 | Buckwheat and products thereof | | x |

[1]The allergens list is based on EU regulation no 1169/2011,
[2]Gluten NMT 20 mg/kg Furthermore, as can be derived from the Examples, the method of the present invention provides compositions with a high amount of colony forming units of the *S. salivarius* strain, i.e. between 3E+11 and 6E+11 CFU/g, preferably about 4E+11 CFU/g. The amount of CFUs is even higher in the process which uses the allergen-free growth medium in comparison to the process which uses whey permeat as protein-source. Furthermore, the compositions are storage stable for fat least 720 day at −20° C. and 4° C.

Such compositions are used for the preparation of probiotic products and pharmaceutical products in any form suitable for human consumption. Thus, the present invention further relates to the use of the composition for producing probiotic and pharmaceutical products, which are selected from but not limited to mouth cream, lotion, gel, ointment, solution, suspension, emulsion, powder, granules, drops, sachet, mouth wash, mouth rinse, toothpaste, dentifrice, spray, gargle, capsule, tablets, lozenge, syrup, floss, film, chewing gum, chewable tablet, food, drink, confectionary, nutraceutical, for example yoghurt, cheese, milk, milk power, milk biscuits, ice cream and flavored milks.

Preferably, the composition of the present invention is used for producing tablets, in particular lozenges or a chewable tablets, chewing gums, capsules, sachets, foods, drinks, confectionaries, or nutraceuticals.

The present invention further relates to a method of producing a probiotic raw material, wherein the method comprises cultivating a *Streptococcus salivarius* strain as explained in detail above with regard to the method of producing a freeze-dried probiotic composition. Furthermore, the method of the present invention comprises harvesting the strain, which can performed as well as mentioned above, for example by filtration or centrifugation, preferably by centrifugally concentrated using a separator.

The invention also relates to the probiotic raw material as obtained by the method of the present invention. Thus, the raw material comprises a *S. salivarius* strain, *S. salivarius* K12, *S. salivarius* ENT-K12, *S. salivarius* M18, or *S. salivarius* M18DF. As mentioned above, the raw material is safe for human consumption and in case the raw material is produced by the method which comprises cultivating the strain in growth medium which does not comprise a milk product, the raw material even free of allergens.

The invention also relates to the use of the probiotic raw material either for producing probiotic/pharmaceutical products, which are selected from but not limited to mouth cream, lotion, gel, ointment, solution, suspension, emulsion, powder, granules, drops, sachet, mouth wash, mouth rinse, toothpaste, dentifrice, spray, gargle, capsule, tablets, lozenge, syrup, floss, film, chewing gum, chewable tablet, food, drink, confectionary, nutraceutical, for example yoghurt, cheese, milk, milk power, milk biscuits, ice cream and flavored milks; or for producing the probiotic composition of the present invention.

The present invention also provides a method of producing a mass culture of the *S. salivarius* strain and a method of cultivating the *S. salivarius* strain, respectively, wherein the method comprises the cultivation steps as defined above in accordance with the method of the present invention for producing the probiotic composition and for producing the probiotic raw material, respectively.

Several documents are cited throughout the text of this specification. The contents of all cited references (including literature references, issued patents, published patent applications as cited throughout this application including the background section and manufacturer's specifications, instructions, etc.) are hereby expressly incorporated by reference; however, there is no admission that any document cited is indeed prior art as to the present invention.

A more complete understanding can be obtained by reference to the following specific Examples which are provided herein for purposes of illustration only and are not intended to limit the scope of the invention.

EXAMPLES

Example 1: Process for Manufacturing a Probiotic Composition Comprising *Streptococcus salivarius*

Raw Materials

The raw materials and processing aids used in the manufacturing of freeze-dried *S. salivarius*K12/ENT-K12 powder are presented below. All ingredients for the fermentation media, processing aids and lyoprotectants are food grade standard and optionally pharmaceutical grade, GMO-free, free of BSE/TSE and meet Halal requirements. Lyoprotectants are allergen free according to EU Regulation 1169/2011.

*S. salivarius* K12 is obtainable for example from the ATCC under Accession number BAA-1024 and *S. salivarius* ENT-K12, which is genetically identical to *S. salivarius* K12 has been deposited at the Leibniz-Institut DSMZ, and assigned Accession Number DSM 34540. The lyoprotectants used in this method are trehalose, lactitol monohydrate and maltodextrin DE19. The raw materials used during fermentation, i.e. cultivation of *S. salivarius* are listed below:

| Raw Material | Purpose |
|---|---|
| Dextrose Monohydrate | Fermentation Ingredient |
| Yeast Extract | Fermentation Ingredient |
| Whey permeat | Fermentation Ingredient |
| Casein peptone | Fermentation Ingredient |
| Di-potassium phosphate | Buffering substance |
| Glanapon | Anti-foaming agent |
| Polysorbate 80 (Liposorb O-20) | Fermentation Ingredient |
| Ammonia solution (25%) | Other processing aid/pH adjusting agent |
| Sodium hydroxide (30%) | Other processing aid/pH adjusting agent |
| Hydrochloride acid (33.8%) | Other processing aid/pH adjusting agent |
| Lactic acid | Other processing aid/pH adjusting agent |

Fermentation Media and Lyoprotectant Preparation

I. Preparation of Fermentation Media

The fermentation medium comprises as fermentation ingredient a mixture of tap water, whey permeat (dissolved in water), yeast extract, casein-peptone, dextrose, di-potassium phosphate and polysorbate 80. In particular, the medium comprises 3-8 g/l yeast extract, 1.5-2.2 g/l di-potassium phosphate, 7-12 g/l dextrose monohydrate, 24-28 g/l whey permeate, 15-20 g/l casein-peptone and 0.5-1.0 g/l polysorbate 80. The media is subsequently sterilized at 121° C. for 20 min.

II. Preparation of the Lyoprotectants

The lyoprotectant ingredients trehalose, lactitol monohydrate and maltodextrin DE19 are mixed in a mixing vessel and then sterilized at 121° C. for 20 min and transferred to a chilled sterile tank. In particular, the lyoprotecants comprise trehalose in a concentration of 1-2 g/L fermentation broth, lactitol monohydrate in a concentration of 0.5-1 g/L fermentation broth, and maltodextrin in a concentration of 3-4 g/L fermentation broth.

Cultivation of *S. salivarius*, Harvesting and Preparation of the Composition

III. Seed Culture

A vial of frozen working stock is thawed and transferred to the a pre-culture of 600 ml (OD 2-4) and cultivated for approx. 20 h, which is transferred to 900 L fermentation vessel and incubated with the fermentation media described above at 33° C. for approx. 18 h (pH-controlled at pH 6.8 to 7.2).

IV. Fermentation and Harvesting

The seed culture is then transferred to the 15000 L fermentation vessel and incubated at 33° C. and pH 7.1 for approximately 16 h. At about 16 hours (when the dextrose concentration reached 15 g/L) the culture is given a pH shock by lowering the pH to 5 using lactic acid over 40 minutes and then raising the pH again to 7.2 over 40 minutes. The DO concentration is kept between 50% and 80% in the first half of the cultivation and the DO concentration is kept between 0% and 50% in the second half of the cultivation.

The culture is centrifugally concentrated using a separator. The *S. salivarius* concentrate is then mixed with the lyoprotectants (i.e., trehalose, lactitol, maltodextrin and deionized water), and the pH of the solution is adjusted to 7.0±0.2 using sodium hydroxide.

V. Freeze-Drying and Homogenization

The mix is poured onto freeze drier trays, frozen and freeze dried. The powder is then milled, homogenized (with spray-dried maltodextrin, C*Dry MD 01915, Cargill) and vacuum packed and stored at −20° C. Samples from every bag are taken to make a composite for QC testing.

The composition of the freeze-dried powder is composed as follows:

| Ingredient | Function | wt % composition |
|---|---|---|
| *Streptococcus salivarius* K12/ENT-K12 | Active ingredient | 25-35% |
| Maltodextrin | Stability of active ingredient | 40-50% |
| Trehalose | Stability of active ingredient | 10% |
| Lactitol | Stability of active ingredient | 5% |
| Moisture | — | 2-5% |
| Total | | 100.0 |

An overview of the manufacturing process is given in FIG. 1.

Example 2: Process for Manufacturing an Allergen-Free Probiotic Composition Comprising *Streptococcus salivarius*

Raw Materials

The raw materials and processing aids used in the manufacturing of freeze-dried *S. salivarius*K12/ENT-K12 powder are presented below. All ingredients for the fermentation media, processing aids and lyoprotectants are food grade standard and optionally pharmaceutical grade, GMO-free, free of BSE/TSE and meet Halal requirements. Lyoprotectants are allergen free according to EU Regulation 1169/2011.

*S. salivarius* K12 is obtainable for example from the ATCC under Accession number BAA-1024 and *S. salivarius* ENT-K12, which is genetically identical to *S. salivarius* K12 has been deposited at the Leibniz-Institut DSMZ, and assigned Accession Number DSM 34540. The lyoprotectants used in this method are trehalose, dextrose, sodium ascorbate and sodium citrate. The raw materials used during fermentation, i.e. cultivation of *S. salivarius* are listed below:

| Raw Material | Purpose |
|---|---|
| Yeast extract | Fermentation Ingredient |
| Di-potassium phosphate | Fermentation Ingredient |
| Polysorbate 80 | Fermentation Ingredient |
| Glanapon | Anti-foaming agent |
| Dextrose Roquette | Fermentation Ingredient |
| Magnesia sulphate | Fermentation Ingredient |
| Manganese sulfate | Fermentation Ingredient |
| Ammonia solution (25%) | Other processing aid/pH adjusting agent |
| Phosphoric acid | Other processing aid/pH adjusting agent |
| Lactic acid | Other processing aid/pH adjusting agent |

Fermentation Media and Lyoprotectant Preparation

I. Preparation of Fermentation Media

The fermentation media comprises a mixture of tap water, yeast extract (dissolved in water), buffer substances and anti-foaming agents. The media is subsequently sterilized at 121° C. for 20 min. Dextrose is sterilized separately.

The fermentation media comprises the following ingredients:

Yeast extract: 17-25 g/l

Di-potassium phosphate: 1.5-2 g/l,

Manganese sulfate: 0.02-0.1 g/l,

Glanapon.: 0.1 g/l,

Polysorbate 80: 0.5-1 g/l,

Dextrose monohydrate: 25-40 g/l, and

Magnesium sulphate: 0.2-0.4 g/l

Manganese sulphate: 0.02-0.1 g/l

II. Preparation of the Lyoprotectants

The lyoprotectant ingredients trehalose, dextrose, sodium ascorbate, sodium citrate and L-cystein are mixed in a mixing vessel and then sterilized at 121° C. for 20 min and transferred to a chilled sterile tank. In particular, the lyoprotectants comprise trehalose in a concentration of 4-7 g/L fermentation broth, dextrose in a concentration of 0.1-0.4 g/L fermentation broth, sodium ascorbate in a concentration of 0.1-0.4 g/L fermentation broth, sodium citrate and L-cysteine in a concentration of 0.2-0.6 g/L fermentation broth.

Cultivation of *S. salivarius*, Harvesting and Preparation of the Composition

III. Seed Culture

A vial of frozen working stock is thawed and transferred to the a pre-culture of 600 ml (OD 2-4) and cultivated for approx. 24 h, which is transferred to 900 L fermentation vessel and incubated with the fermentation media described above at 33° C. for approx. 14 h (pH-controlled at pH 6.8 to 7.2).

IV. Fermentation and Harvesting

The seed culture is then transferred to the 15000 L fermentation vessel and incubated at 33° C. and pH 7.1 for approx. 10 h. At about 8 hours (when the dextrose concentration reached 15 g/L) the culture is given a pH shock by lowering the pH to 5.3 using lactic acid over 1 hour and then raising the pH again to 6.8 until end of fermentation. The DO concentration is kept between 50% and 80% in the first half of the cultivation and the DO concentration is kept between 0% and 50% in the second half of the cultivation.

The culture is centrifugally concentrated using a separator. The *S. salivarius* concentrate is then mixed with the lyoprotectants (i.e., trehalose at a concentration of 4-7 g/L fermentation broth, dextrose at a concentration of 0.1-0.4 g/L fermentation broth, sodium ascorbate at a concentration of 0.1-0.4 g/L fermentation broth, sodium citrate and L-cystein at a concentration of 0.2-0.6 g/L fermentation broth), and the pH of the solution is adjusted to 7.0±0.2 using sodium hydroxide.

V. Freeze-Drying and Homogenization

The mix is poured onto freeze drier trays, frozen and freeze dried. The powder is then milled, homogenized (with spray-dried maltodextrin, C*Dry MD 01915, Cargill) and vacuum packed and stored at −20° C. Samples from every bag are taken to make a composite for QC testing.

The composition of the freeze-dried powder is composed of at least the following ingredients:

| Ingredient | Function | wt % composition |
|---|---|---|
| *Streptococcus salivarius* K12/ENT-K12 | Active ingredient | 32-40% |
| Trehalose | Stability of active ingredient | 50-60% |
| Dextrose | Stability of active ingredient | 2-3% |
| Sodium ascorbate | Stability of active ingredient | 2-3% |
| Sodium citrate | Stability of active ingredient | 2-3% |
| Moisture | — | 2-5% |
| Total | | 100.0 |

An overview of the manufacturing process is given in FIG. 2.

Example 3: Determination of Cell Number and Stability Data of the Freeze-Dried Probiotic Composition In order to verify the stability of the probiotic powder composition, the cell number has been determined in different batches (sts) during storage of the composition at different temperatures, i.e. at −20° C., 4° C. and 20° C., wherein exemplarily batches are shown in Table 3. In this context, the compositions which have been produced by the method of the present invention using growth medium which comprises whey permeat have been compared to compositions which have been produced by the method of the present invention using growth medium which does not comprise whey permeat (hypoallergenic culture technology).

Determination of CFUs of *S. salivarius* has been performed as described in "Istituto Superiore di Sanità, Metodi microbiologici tradizionali e metodi molecolari per l'analisi degli integratori alimentari a base di o con, probiotici per uso umano, by Paolo Aureli, Alfonsina Fiore, Concetta Scalfaro, Giovanna Franciosa, 2008, ii, 63 p. Rapporti ISTISAN 08/36, ISSN 1123-3117", in particular in chapter 24. The results are listed in Table 3.

TABLE 3

Cell numbers of different batches (sts) of the probiotic powder composition during storage at different temperatures. The compositions have been prepared by the method of the present invention using growth medium which comprises whey permeat and by the method of the present invention using growth medium which does not comprise whey permeat (hypoallergenic culture technology).

| Presence of whey permeat | | | | |
|---|---|---|---|---|
| Temp | | | Absence of whey permeat (hypoallergen) | |
| ° C. | days | sts#14 | sts#59 | sts#56 |
| −20 | 0 | 3.21E+11 | 3.89E+11 | 6.03E+11 |
| −20 | 30 | 3.09E+11 | 3.41E+11 | 7.20E+11 |
| −20 | 90 | 2.30E+11 | 3.92E+11 | 6.63E+11 |
| −20 | 180 | 3.25E+11 | 3.96E+11 | 6.20E+11 |
| −20 | 365 | 3.34E+11 | | |
| −20 | 540 | 2.69E+11 | | |

TABLE 3-continued

Cell numbers of different batches (sts) of the probiotic powder composition during storage at different temperatures. The compositions have been prepared by the method of the present invention using growth medium which comprises whey permeat and by the method of the present invention using growth medium which does not comprise whey permeat (hypoallergenic culture technology).

| Temp | Presence of whey permeat | | Absence of whey permeat (hypoallergen) | |
|---|---|---|---|---|
| ° C. | days | sts#14 | sts#59 | sts#56 |
| −20 | 720 | 2.85E+11 | | |
| 4 | 0 | 3.21E+11 | 3.89E+11 | 6.03E+11 |
| 4 | 30 | 2.55E+11 | 3.37E+11 | 6.67E+11 |
| 4 | 90 | 3.16E+11 | 3.18E+11 | 6.20E+11 |
| 4 | 180 | 3.18E+11 | 3.09E+11 | 4.67E+11 |
| 4 | 365 | 2.78E+11 | | |
| 4 | 540 | 2.31E+11 | | |
| 4 | 720 | 2.33E+11 | | |
| 20 | 0 | 3.21E+11 | 3.89E+11 | 6.03E+11 |
| 20 | 30 | 2.32E+11 | 3.12E+11 | 4.30E+11 |
| 20 | 90 | 2.23E+11 | 2.39E+11 | 3.47E+11 |
| 20 | 180 | 1.94E+11 | 1.52E+11 | 1.55E+11 |
| 20 | 365 | 1.72E+11 | | |
| 20 | 540 | 1.53E+11 | | |
| 20 | 720 | 8.93E+10 | | |

As can be derived from Table 3, the compositions are storage stable and the number of CFUs is even higher in compositions which have been produced with the hypoallergenic culture technology.

Example 4: Ascorbate as Stabilizer in a Process for Manufacturing a Probiotic Composition Comprising *Streptococcus salivarius*

In a further experiment, ascorbate was used as growth medium supplement in the process for producing a probiotic composition. In particular, the process was performed as described in Example 2, but wherein ascorbic acid was added to the growth medium as fermentation ingredient (which converts to ascorbate when the medium is pH adjusted) so that ascorbate was present in the growth medium in the amount of 0.3-0.5 g/l.

In order to verify the stability of the probiotic powder composition, the cell number has been determined in different batches (sts) during storage of the composition at different temperatures, i.e. at −20° C., 4° C. and 20° C., wherein an exemplarily batch stored at 4° C. is shown in Table 4. In this context, the composition which has been produced by the method of the present invention using growth medium which comprises ascorbate has been compared to a composition which has been produced by the method of the present invention using growth medium which does not comprise ascorbate.

Determination of CFUs of *S. salivarius* has been performed as described in Example 2.

TABLE 4

Cell numbers of a batch of the probiotic powder composition during storage at 4° C. The compositions have been prepared by the method of the present invention using growth medium which comprises ascorbate and by the method of the present invention using growth medium which does not comprise ascorbate.

| Batch sts#71 4° C. Days | without ascorbate cfu/g | with ascorbate cfu/g |
|---|---|---|
| 0 | 3.42E+11 | 3.25E+11 |
| 30 | 2.43E+11 | 2.93E+11 |
| 90 | 2.19E+11 | 2.61E+11 |
| 180 | 1.87E+11 | 2.51E+11 |

As can be derived from Table 4, the compositions are storage stable and the number of CFUs is even higher in compositions which have been produced with the growth medium comprising ascorbate.

The invention claimed is:

1. A method of producing a probiotic raw material, wherein the method comprises at least the following steps:

(i) cultivating *Streptococcus salivarius* in a growth medium comprising dextrose as a carbon source at a concentration of about 25 to 40 g/L when cultivation begins, wherein the growth medium has a pH of 6.8 to 7.2;

(ii) lowering the pH to pH 5 to 5.5 by adding a pH lowering agent when the concentration of dextrose reaches 10-15 g/L and raising the pH after 30 minutes to 3 hours to pH 6.8 to 7.2 until cultivation ends; and (iii) harvesting the *Streptococcus salivarius*.

2. The method of claim 1, wherein the method further comprises the steps of: (a) concentrating the culture; (b) mixing the concentrated culture with lyoprotectants; (c) freeze drying the mixture; and optionally (d) milling and homogenizing the mixture.

3. The method of claim 2, wherein the lyoprotectants are a mixture comprising trehalose, lactitol monohydrate, and maltodextrin; or a mixture comprising trehalose, dextrose, sodium ascorbate, sodium citrate, and L-cystein.

4. The method of claim 2, comprising adjusting the pH of the mixture in step (b) to about 6.8 to 7.2.

5. The method of claim 1, wherein the growth medium further comprises a milk product.

6. The method of claim 5, wherein the milk product is whey.

7. The method of claim 5, wherein the growth medium further comprises yeast extract, casein-peptone, an emulsifier, a buffering agent, and/or a de-foaming agent.

8. The method of claim 7, wherein the emulsifier is polysorbate 80 and the buffering agent is di-potassium phosphate.

9. The method of claim 1, wherein the growth medium does not comprise a milk product.

10. The method of claim 9, wherein the growth medium comprises yeast extract, an emulsifier, a buffering agent, magnesium sulfate, manganese sulfate, and/or a de-foaming agent.

11. The method of claim 10, wherein the emulsifier is polysorbate 80 and the buffering agent is di-potassium phosphate.

12. The method according to claim 1, wherein the *Streptococcus salivarius* is *Streptococcus salivarius* K12, *Streptococcus salivarius* ENT-K12, *Streptococcus salivarius* M18, or *S. salivarius* M18DF.

13. The method of claim 1, wherein the pH lowering agent is lactic acid.

14. The method of claim 1, wherein the pH during cultivation in step (i) is about 7.1.

15. A probiotic raw material obtainable by the method of claim 1.

16. A method of cultivating *Streptococcus salivarius*, wherein the method comprises at least the following steps:

(i) cultivating *Streptococcus salivarius* in a growth medium comprising dextrose as a carbon source at a concentration of about 25 to 40 g/L when cultivation begins, wherein the growth medium has a pH 6.8 to 7.2; and (ii) lowering the pH to pH 5 to 5.5 by adding a pH lowering agent when the concentration of dextrose reaches 10-15 g/L and raising the pH after 30 minutes to 3 hours to pH 6.8 to 7.2 until cultivation ends.

17. The method of claim 16, wherein the growth medium:

(i) further comprises a milk product; or (ii) does not comprise a milk product.

18. The method of claim 17, wherein the growth medium in (i) further comprises yeast extract, casein-peptone, an emulsifier, a buffering agent, and/or a de-foaming agent, or in (ii) further comprises yeast extract, an emulsifier, a buffering agent, magnesium sulfate, manganese sulfate, and/or a de-foaming agent.

19. The method of claim 18, wherein the emulsifier is polysorbate 80 and the buffering agent is di-potassium phosphate.

20. The method of claim 16, wherein the *Streptococcus salivarius* is selected from the group consisting of *Streptococcus salivarius* K12, ENT-K12, M18, and M18DF.

21. The method of claim 16, wherein the pH during cultivation in step (i) is about 7.1.

22. A method for producing a probiotic composition comprising *Streptococcus salivarius*, or for producing a probiotic raw material comprising *Streptococcus salivarius*, using an allergen-free medium which does not comprise a milk product, the method comprising:

(i) cultivating *Streptococcus salivarius* in a growth medium comprising yeast extract and dextrose, wherein dextrose is present at a concentration of about 25 to 40 g/L when cultivation begins, wherein the growth medium has a pH of 6.8 to 7.2; and (ii) lowering the pH to pH 5 to 5.5 by adding a pH lowering agent when the concentration of dextrose reaches 10-15 g/L and raising the pH after 30 minutes to 3 hours to pH 6.8 to 7.2 until cultivation ends.

23. The method of claim 22, wherein the *Streptococcus salivarius* is selected from the group consisting of *Streptococcus salivarius* K12, ENT-K12, M18, and M18DF.

24. The method of claim 22, wherein the growth medium further comprises a buffering agent, an emulsifier, magnesium sulfate, manganese sulfate, and/or an anti-foaming agent.

25. The method of claim 24, wherein the emulsifier is polysorbate 80 and the buffering agent is di-potassium phosphate.

* * * * *